United States Patent [19]

Friebe et al.

[11] Patent Number: 4,721,717
[45] Date of Patent: Jan. 26, 1988

[54] α-(AMINOALKYLAMINOMETHYL)-PHENYLMETHANOLS, COMPOSITION CONTAINING THEM, AND USE THEREOF TO TREAT CERTAIN HEART AND CIRCULATORY DISEASES

[75] Inventors: Walter-Gunar Friebe, Darmstadt; Wolfgang Kampe, Heddesheim; Erwin Böhm, Schriesheim; Klaus Strein, Hemsbach, all of Fed. Rep. of Germany

[73] Assignee: Boehringer Mannheim GmbH, Mannheim, Fed. Rep. of Germany

[21] Appl. No.: 760,128

[22] Filed: Jul. 29, 1985

[30] Foreign Application Priority Data

Aug. 2, 1984 [DE] Fed. Rep. of Germany ....... 3428526

[51] Int. Cl.$^4$ ................. A61K 31/415; A61K 31/505; C07D 235/30; C07D 239/10
[52] U.S. Cl. .................................... 514/274; 514/388; 514/394; 514/395; 514/404; 514/405; 514/407; 514/415; 514/532; 514/533; 514/539; 514/605; 514/653; 544/312; 548/305; 548/306; 548/325; 548/329; 548/358; 548/359; 548/362; 548/371; 548/372; 548/375; 548/469; 548/483; 560/13; 560/18; 564/83; 564/99; 564/363
[58] Field of Search ................. 544/312; 548/483, 371, 548/372, 359, 305, 306, 325, 329, 358, 362, 375, 469; 560/13, 18, 48; 564/85, 86, 363, 83, 99; 514/274, 415, 405, 388, 394, 395, 407, 532, 533, 539, 605, 653, 404

[56] References Cited

U.S. PATENT DOCUMENTS 4,304,790 12/1981 Neustadt et al. ............... 514/653
4,438,128 3/1984 Wiedemann et al. ............ 514/415

Primary Examiner—Henry R. Jiles
Assistant Examiner—Kurt G. Briscoe
Attorney, Agent, or Firm—Felfe & Lynch

[57] ABSTRACT

The present invention provides aminoalcohols of the general formula:

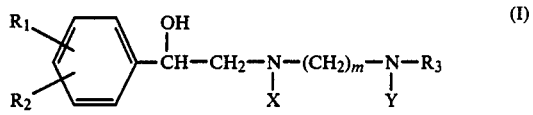

wherein $R_1$ and $R_2$, which can be same or different, are hydrogen atoms, hydroxyl groups, $C_1$–$C_4$-alkoxy, benzyloxy, $C_1$–$C_4$-alkoxycarbonyl, $C_1$–$C_4$-alkanesulphonylamino, $C_1$–$C_4$-alkanesulphinyl or $C_1$–$C_4$-alkanesulphonyl radicals, m is 2, 3 or 4, X and Y, which can be the same or different, are hydrogen atoms or benzyl radicals and $R_3$ is a phenyl radical substituted twice by $C_1$–$C_6$-alkyl radicals, a nitrophenyl radical, an aminophenyl radical, a 1,3,5-tri-$C_1$–$C_6$-alkyl-2,4-dioxo-1H,3H-pyrimidin-6-yl radical, an indolyl radical, an indazolyl radical, a benzimidazolyl radical, a 1,4-di-$C_1$–$C_6$-alkylpyrazol-5-yl radical or a radical of the general formula:

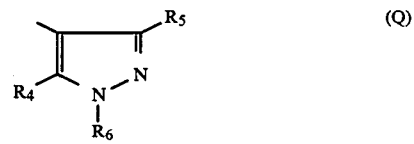

wherein $R_4$ and $R_5$, which can be the same or different, are $C_1$–$C_4$-alkyl radicals and $R_6$ is a $C_1$–$C_6$-alkyl, $C_2$–$C_6$-alkenyl, phenyl or benzyl radical; and the pharmacologically acceptable salts there, as well as methods for making and using these compounds and compositions containing them. There are useful as cardiovascular medicaments.

15 Claims, No Drawings

α-(AMINOALKYLAMINOMETHYL)PHENYLMETHANOLS, COMPOSITION CONTAINING THEM, AND USE THEREOF TO TREAT CERTAIN HEART AND CIRCULATORY DISEASES

The present invention is concerned with new aminoalcohols, processes for the preparation thereof and pharmaceutical compositions containing them.

The compounds according to the present invention possess a significant action on the deformability of erythrocytes and improve the flowability of the blood. Therefore, they can be used especially for the treatment of peripheral, cerebral and coronary blood flow disturbances. Furthermore, they display a positive inotropic action.

The new aminoalcohols according to the present invention are compounds of the general formula:

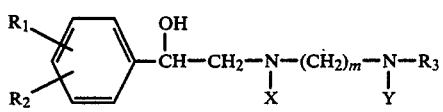 (I)

wherein $R_1$ and $R_2$, which can be the same or different, are hydrogen atoms, hydroxyl groups or $C_1-C_4$-alkoxy, benzyloxy, $C_1-C_4$-alkoxycarbonyl, $C_1-C_4$-alkanesulphonamido, $C_1-C_4$-alkanesulphinyl or $C_1-C_4$-alkanesulphonyl radicals, m is 2, 3 or 4, X and Y, which can be the same or different, are hydrogen atoms or benzyl radicals and $R_3$ is a phenyl radical substituted twice by $C_1-C_4$-alkyl radicals, a nitrophenyl radical, an aminophenyl radical, a 1,3,5-tri-$C_1-C_6$-alkyl-2,4-dioxo-1H,3H-pyrimidin-6-yl radical, an indolyl radical, an indazolyl radical, a benzimidazolyl radical, a 1,4-di-$C_1-C_6$-alkylpyrazol-5-yl radical or a radical of the general formula:

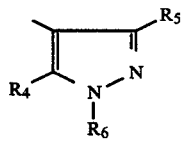 (Q)

wherein $R_4$ and $R_5$, which can be the same or different, are $C_1-C_4$-alkyl radicals and $R_6$ is a $C_1-C_6$-alkyl, $C_2-C_6$-alkenyl, phenyl or benzyl radical; as well as the pharmacologically acceptable salts thereof.

Apart from the compounds mentioned hereinafter in the specific Examples, the present invention also provides all compounds which have every possible combination of the substituents mentioned in the Examples.

The new compounds of general formula (I) according to the present invention can be prepared in known manner by reacting a compound of the general formula:

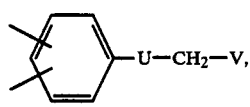 (II)

in which $R_1$ and $R_2$ have the above-given meaning, V is a reactive residue and U is a >C=O or >CH—Z group, Z being a hydroxyl group or, together with V, representing an oxygen atom, with a compound of the general formula:

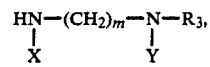 (III)

in which X, Y, m and $R_3$ have the above-given meanings, and, when U is a >C=O group, the product obtained is subsequently reduced and when X and/or Y stands for a benzyl radical, this is, if desired, split off, a radical $R_1$ or $R_2$ is, if desired, changed into another radical $R_1$ and $R_2$ and the compound thus obtained is, if desired, converted into a pharmacologically acceptable salt.

The intermediates obtained of the general formula:

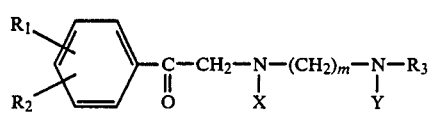 (Ia)

in which $R_1$, $R_2$, m, X, Y and $R_3$ have the above-given meanings, are also new and part of the subject matter of the present invention.

The reactive residue V in compounds of general formula (II) can be a chlorine or bromine atom or a mesyloxy or tosyloxy radical.

The process according to the present invention is preferably carried out in a solvent which is inert under the reaction conditions, for example, toluene, dioxan, tetrahydrofuran, ethylene glycol dimethyl ether, ethanol, butanol, acetone or dimethylformamide, possibly in the presence of an acid-binding agent. Mixtures of the above-mentioned solvents can also be used.

The reduction possibly to be carried out when R stands for a >C=O group can be carried out by means of complex metal hydrides, for example sodium borohydride, or by catalytic hydrogenation in the presence of noble metal catalysts.

The splitting off of a benzyl radical X and Y is preferably carried out with the use of catalytically-activated hydrogen.

A subsequent conversion of a radical $R_1$ or $R_2$ into another radical $R_1$ and $R_2$ can be, for example, a hydrogenolytic conversion of a benzyl radical into a hydroxyl group.

The compounds of general formulae (II) and (III) are either known from the literature or can be prepared by known methods from materials known from the literature (cf. Federal Republic of Germany Patent Specifications Nos. 30 23 369 and 31 31 146).

For the conversion of compounds of general formula (I) into their pharmacologically acceptable salts, they are reacted, preferably in an organic solvent, with an inorganic or organic acid, for example hydrochloric acid, hydrobromic acid, phosphoric acid, sulphuric acid, acetic acid, citric acid, tartaric acid, maleic acid, fumaric acid, benzoic acid or oxalic acid.

The compounds of general formula (I) according to the present invention can be obtained in the form of a racemic mixture. The resolution of the racemate into the optically-active forms takes place in known manner via diastereomeric of optically-active acids, for example tartaric acid, malic acid or camphorsulphonic acid.

For the preparation of pharmaceutical compositions, the compounds of general formula (I) are mixed in known manner with appropriate pharmaceutical carrier substances, aroma, flavouring and colouring materials and formed, for example, into tablets or dragees or, with the addition of appropriate adjuvants, suspended or dissolved in water or in an oil, for example olive oil.

The new compounds of general formula (I) according to the present invention and the salts thereof can be administered enterally or parenterally. As injection medium, it is preferred to use water which contains the additives usual in the case of injection solutions, such as stabilising agents, solubilising agents or buffers.

Such additives include, for example, tartrate and citrate buffers, ethanol, complex formers (such as ethylenediamine-tetraacetic acid and the non-toxic salts thereof) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening agents.

The dosage administered depends upon the age, state of health and weight of the recipient, the extent of the disease, the nature of possibly simultaneously carried out other treatments, the frequency of the treatment and the nature of the desired action. The daily dosage of the active compound is usually 0.1 to 50 mg./kg. of body weight. Normally, 0.5 to 40 and preferably 1.0 to 20 mg./kg./day in one or more administrations are effective for obtaining the desired results.

Preferred compounds according to the present invention, apart from those described in the following Examples, include the following:

2-hydroxy-5-{1-hydroxy-2-[2-(2,6-dimethyl-phenylamino)-ethylamino]-ethyl}-benzenesulphonamide N-[2-hydroxy-5-{1-hydroxy-2-[2-(2,6-dimethyl-phenylamino)-ethylamino]-ethyl}-phenyl]-methanesulphonamide 4-hydroxy-3-methylsulphinyl-α-{[2-(2,6-dimethyl-phenylamino)-ethyl]-aminomethyl}-phenylmethanol 4-hydroxy-3-methylsulphonyl-α-{[2-(2,6-dimethyl-phenylamino)-ethyl]-aminomethyl}-phenylmethanol 3-hydroxy-α-{[2-(3-nitrophenylamino)-ethyl]-aminomethyl}-phenylmethanol 4-hydroxy-α-{[2-(3-nitrophenylamino)-ethyl]-aminomethyl}-phenylmethanol 3-hydroxy-α-{[2-(2,4-dioxo-1,3,5-trimethyl-1H,3H-pyrimidin-6-ylamino)-ethyl]-aminomethyl}-phenylmethanol α-{[2-(1-allyl-3,5-dimethylpyrazol-4-ylamino)-ethyl]-aminomethyl}-phenylmethanol 3-hydroxy-α-{[2-(1-allyl-3,5-dimethylpyrazol-4-ylamino)-ethyl]-aminomethyl}-phenylmethanol 4-hydroxy-α-{[2-(1-allyl-3,5-dimethylpyrazol-4-ylamino)-ethyl]-aminomethyl}-phenylmethanol α-{[2-(1-phenyl-3,5-dimethylpyrazol-4-ylamino)-ethyl]-aminomethyl}-phenylmethanol α-{[2-(1-benzyl-3,5-dimethylpyrazol-4-ylamino)-ethyl]-aminomethyl}-phenylmethanol.

The following Examples are given for the purpose of illustrating the present invention:

EXAMPLE 1

α-{[2-(3-Nitrophenylamino)-ethyl]-aminomethyl}-phenylmethanol

A mixture of 3.0 g. (25 mMole) styrene oxide, 9.0 g. (50 mMole) N-(3-nitrophenyl)-1,2-diaminoethane and 25 ml. n-butanol is stirred at ambient temperature for 3 hours. The reaction mixture is mixed with 100 ml. diethyl ether and the precipitate is filtered off and recrystallised from ethyl acetate. There are obtained 3.9 g. (52% of theory) α-{[2-(3-nitrophenylamino)-ethyl]-aminomethyl}-phenylmethanol; m.p. 141°–142° C.

EXAMPLE 2

The following compounds are obtained in the form of oils in a manner analogous to that described in Example 1:

|     | designation | yield % |
| --- | --- | --- |
| (a) | 2-benzyloxy-α-{[2-(2,6-dimethyl-phenylamino)-ethyl]-aminomethyl}-phenylmethanol from 2-benzyloxystyrene oxide and N—(2,6-dimethylphenyl)-1,2-diaminoethane | 59 |
| (b) | 2-methoxy-α-{[2-(2,6-dimethyl-phenylamino)-ethyl]-N—benzylaminomethyl}-phenylmethanol from 2-methoxystyrene oxide and N—[2-(2,6-dimethylphenylamino)-ethyl]-benzylamine | 29 |

EXAMPLE 3

4-Benzyloxy-α-{[2-(2,6-dimethylphenylamino)-ethyl]-aminomethyl}-phenylmethanol 9.6 g. (0.24 mole) sodium borohydride are added at 0° C., within the course of 10 minutes, to a solution of 33.8 g. (80 mMole) 1-(4-benzyloxyphenyl)-2-[2-(2,6dimethylphenylamino)-ethylamino]-ethane in 600 ml. ethanol. The reaction mixture is further stirred for 1 hour at 0° C., poured on to ice, acidified with dilute acetic acid, mixed with excess sodium hydrogen carbonate solution and extracted with dichloromethane. After evaporation of the extracts, there are obtained 28.9 g. (87% of theory) 4-benzyloxy-α-{[2-(2,6-dimethylphenylamino)-ethyl]-aminomethyl}-phenylmethanol in the form of an oil.

EXAMPLE 4

The following compounds are obtained in the form of oils in a manner analogous to that described in Example 3.

|     | designation | yield % |
| --- | --- | --- |
| (a) | 3-benzyloxy-α-{[2-(2,6-dimethyl-phenylamino)-ethyl]-aminomethyl}-phenylmethanol from 1-(3-benzyloxyphenyl)-2-[2-(2,6-dimethylphenylamino)-ethylamino]-ethanone | 45 |
| (b) | α-{[2-(2,6-dimethylphenylamino)-ethyl]-N—benzylaminomethyl}-phenyl-methanol from 2-[2-(2,6-dimethylphenylamino)-ethyl-N—benzylamino]-1-phenyl-ethanone | 84 |
| (c) | 4-benzyloxy-3-methoxy-α-{[2-(2,6- | 71 |

-continued

| | designation | yield % |
|---|---|---|
| | dimethylphenylamino)-ethyl]-N—benzylaminomethyl}-phenylmethanol from 1-(4-benzyloxy-3-methoxyphenyl)-2-[2-(2,6-dimethylphenylamino)-ethyl-N—benzylamino]-ethanone | |
| (d) | 3,5-dibenzyloxy-α-{[2-(2,6-dimethylphenylamino)-ethyl]-N—benzylaminomethyl}-phenylmethanol from 1-(3,5-dibenzyloxyphenyl)-2-[2-(2,6-dimethylphenylamino)-ethyl-N—benzylamino-ethanone | 55 |
| (e) | α-{[3-(2,6-dimethylphenylamino)-propyl]-N—benzylaminomethyl}-phenylmethanol from 2-[3-(2,6-dimethylphenylamino)-propyl-N—benzylamino]-1-phenyl-ethanone | 76 |
| (f) | 4-benzyloxy-α-{[3-(2,6-dimethyl-phenylamino)-propyl]-N—benzylaminomethyl}-phenylmethanol from 1-(4-benzyloxyphenyl)-2-[3-(2,6-dimethylphenylamino)-propyl-N—benzylamino]-ethanone | 68 |
| (g) | 3-benzyloxy-α-[{2-(1,3,5-trimethyl-pyrazol-4-yl)-N—benzylamino]-ethyl}-N—benzylaminomethyl]-phenylmethanol from 1-(3-benzyloxyphenyl)-2-{2-[1,3,5-trimethylpyrazol-4-yl)-N—benzyl-amino]-ethyl-N—benzylamino}-ethanone | 62 |
| (h) | 4-benzyloxy-α-[{2-[(1,3,5-trimethyl-pyrazol-4-yl)-N—benzylamino]-ethyl}-N—benzylaminomethyl]-phenylmethanol from 1-(4-benzyloxyphenyl)-2-{2-[(1,3,5-trimethylpyrazol-4-yl)-N—benzyl-amino]-ethyl-N—benzylamino}-ethanone | 55 |
| (i) | α-[{2-[(1,3,5-trimethylpyrazol-4-yl)-N—benzylamino]-ethyl}-N—benzylamino-methyl]-phenylmethanol from 1-phenyl-2-{2-[(1,3,5-trimethyl-pyrazol-4-yl)-N—benzylamino]-ethyl-N—benzylamino}-ethanone | 45 |
| (j) | 3-benzyloxy-α-{[2-(1,4-dimethyl-pyrazol-5-ylamino)-ethyl]-N—benzyl-aminomethyl}-phenylmethanol from 1-(3-benzyloxyphenyl)-2-[2-(1,4-dimethylpyrazol-5-ylamino)-ethyl-N—benzylamino]-ethanone | 38 |
| (k) | 4-benzyloxy-α-{[2-(1.4-dimethyl-pyrazol-5-ylamino)-ethyl]-N—benzylaminomethyl}-phenylmethanol from 1-(4-benzyloxyphenyl)-2-[2-(1,4-dimethylpyrazol-5-ylamino)-ethyl-N—benzylamino]-ethanone | 43 |
| (l) | 3-benzyloxy-α-{[2-(indazol-4-yl-amino)-ethyl]-aminomethyl}-phenyl-methanol from 1-(3-benzyloxyphenyl)-2-[2-(indazol-4-ylamino)-ethylamino]-ethanone | 35 |
| (m) | 4-benzyloxy-α-{[2-(indazol-4-yl-amino)-ethyl]-N—benzylaminomethyl}-phenylmethanol from 1-(4-benzyloxyphenyl)-2-[2-indazol-4-ylamino)-ethyl-N—benzyl-amino]-ethanone | 88 |

EXAMPLE 5

α-{[2-(2,6-Dimethylphenylamino)-ethyl]-aminomethyl}-2-hydroxyphenylmethanol

A solution of 6.8 g. (18 mMole) 2-benzyloxy-α-{[2-(2,6-dimethylphenylamino)-ethyl]-aminomethyl}-phenylmethanol (compound of Example 2a)) in 100 ml. ethanol and 10 ml. water is hydrogenated at ambient temperature and 1 bar hydrogen pressure in the presence of 1 g. 10% palladium-charcoal. The reaction mixture is then filtered, the filtrate is evaporated and the residue is taken up in acetone and mixed with the calculated amount of oxalic acid. After recrystallisation from acetone, there are obtained 5.4 g. of the oxalate of α-{[2-(2,6-dimethylphenylamino)-ethyl]-aminomethyl}-2-hydroxyphenylmethanol; m.p. 112°–113° C.

EXAMPLE 6

The following compounds are obtained in a manner analogous to that described in Example 5:

| | designation | yield % | melting point (solvent) |
|---|---|---|---|
| (a) | α-{[2-(2,6-dimethylphenyl-amino)-ethyl]-aminomethyl}-2-methoxyphenylmethanol from the compound of Example 2 b | 83 | oxalate 186–188° C. (2-propanol) |
| (b) | α-{[2-(2,6-dimethylphenyl-amino)-ethyl]-aminomethyl}-4-hydroxy-phenylmethanol from the compound of Example 3 | 54 | 159–160° C. (diethyl ether) |
| (c) | α-{[2-(2,6-dimethylphenyl-amino)-ethyl]-aminomethyl}-3-hydroxyphenylmethanol from the compound of Example 4 a | 65 | oxalate 85–90° C. (amorphous) |
| (d) | α-{[2-(2,6-dimethylphenyl-amino)-ethyl]-aminomethyl}-phenylmethanol from the compound of Example 4 b | 43 | 88–90°C. (2-propanol) |
| (e) | α-{[2-(2,6-dimethylphenyl-amino)-ethyl]-aminomethyl}-4-hydroxy-3-methoxyphenyl-methanol from the compound of Example 4 c | 56 | hydrochloride 168–170° C. (ethanol) |
| (f) | 3,5-dihydroxy-α-{[2-(2,6-dimethylphenylamino)-ethyl]-aminomethyl}-phenylmethanol from the compound of Example 4 d | 75 | hydrochloride 100–110° C. (amorphous) (ethyl acetate) |
| (g) | α-{[3-(2,6-dimethylphenyl-amino)-propyl]-aminomethyl}-phenylmethanol from the compound of Example 4 e | 85 | 93–94° C. (2-propanol) |
| (h) | α{[3-(2,6-dimethylphenyl-amino)-propyl]-aminomethyl}-4-hydroxyphenylmethanol from the compound of Example 4 f | 76 | 148–150° C. (2-propanol) |
| (i) | 3-hydroxy-α-{[2-(1,3,5-trimethylpyrazol-4-ylamino)-ethyl]-aminomethyl}-phenyl-methanol from the compound of Example 4 g | 48 | hydrochloride 65–70° C. (amorphous) (2-propanol) |
| (j) | 4-hydroxy-α{[2-(1,3,5-trimethylpyrazol-4-ylamino)-ethyl]-aminomethyl}-phenyl-methanol from the compound of Example 4 h | 45 | 162–164° C. (diethyl ether) |
| (k) | α-{[2-(1,3,5-trimethylpyrazol-4-ylamino)-ethyl]-aminomethyl}-phenylmethanol from the compound of Example 4 i | 51 | dihydrochloride 75–80° C. (amorphous) |
| (l) | α-{[2-(1,4-dimethylpyrazol-5-ylamino)-ethyl]-aminomethyl}-3-hydroxyphenylmethanol from the compound of Example 4 j | 60 | dimaleate 146–149° C. (acetone) |
| (m) | α-{[2-(1,4-dimethylpyrazol-5-ylamino)-ethyl]-aminomethyl}-4-hydroxyphenylmethanol from the compound of Example 4 k | 77 | dimaleate 142–144° C. (acetone) |
| (n) | 3-hydroxy-α-{[2-(indazol-4-ylamino)-ethyl]-aminomethyl}-phenylmethanol from the compound of Example 4 l | 93 | 90–95° C. (amorphous) (diethyl ether) |

| designation | yield % | melting point (solvent) |
|---|---|---|
| (o) 4-hydroxy-α-{[2-(indazol-4-ylamino)-ethyl]-aminomethyl}-phenylmethanol from the compound of Example 4 m | 82 | 89–90° C. (amorphous) (diethyl ether) |

EXAMPLE 7

The 1-(4-benzyloxyphenyl)-2-[2-(2,6-dimethylphenylamino)-ethylaminoe]-ethanone used as intermediate in Example 3 can be prepared in the following manner:

A mixture of 6.6 g. (40 mMole) 2-(2,6-dimethylphenylamino)-ethylamine, 12.2 g. (40 mMole) 4-benzyloxyphenacyl bromide, 150 ml. tetrahydrofuran and 5.1 g. triethylamine is stirred at ambient temperature for 3 hours. The reaction mixture is then filtered and the filtrate is evaporated to give 15.3 g. (99% of theory) 1-(4-benzyloxyphenyl)-2-[2-(2,6-dimethylphenylamino)-ethylamino]-ethanone in the form of an oil.

EXAMPLE 8

The following compounds are obtained in the form of oils in a manner analogous to that described in Example 7:

| designation | yield % |
|---|---|
| (a) 1-(3-benzyloxyphenyl)-2-[2-(2,6-dimethylphenylamino)-ethylamino]-ethanone from 2-(2,6-dimethylphenylamino)-ethylamine and 3-benzyloxyphenacyl bromide | 96 |
| (b) 2-[2-(2,6-dimethylphenylamino)-ethyl-N—benzylamino]-1-phenyl-ethanone from N—[2-(2,6-dimethylphenylamino)-ethyl]-benzylamine and phenacyl bromide | 97 |
| (c) 1-(4-benzyloxy-3-methoxyphenyl)-2-[2-(2,6-dimethylphenylamino)-ethyl-N—benzylamino]-ethanone from N—[2-(2,6-dimethylphenylamino)-ethyl]-benzylamine and 4-benzyloxy-3-methoxyphenacyl bromide | 98 |
| (d) 1-(3,5-dibenzyloxyphenyl)-2-[2-(2,6-dimethylphenylamino)-ethyl-N—benzylamino]-ethanone from N—[2-(2,6-dimethylphenylamino)-ethyl]-benzylamine and 3,5-dibenzyloxyphenacyl bromide | 95 |
| (e) 2-[3-(2,6-dimethylphenylamino)-propyl-N—benzylamino]-1-phenyl-ethanone from N—[3-(2,6-dimethylphenylamino)-propyl]-benzylamine and phenacyl bromide | 100 |
| (f) 1-(4-benzyloxyphenyl)-2-[3-(2,6-dimethylphenylamino)-propyl-N—benzylamino]-ethanone from N—[3-(2,6-dimethylphenylamino)-propyl]-benzylamine and 4-benzyloxyphenacyl bromide | 95 |
| (g) 1-(3-benzyloxyphenyl)-2-{2-[(1,3,5-trimethylpyrazol-4-yl)-N—benzylamino]-ethyl-N—benzylamino}-ethanone from N—{2-[(1,3,5-trimethylpyrazol-4-yl)-N—benzylamino]-ethyl}-benzylamine and 3-benzyloxyphenacyl bromide | 95 |
| (h) 1-(4-benzyloxyphenyl)-2-{2-[(1,3,5-trimethylpyrazol-4-yl)-N—benzylamino]-ethyl-N—benzylamino}-ethanone from N—{2-[(1,3,5-trimethylpyrazol-4-yl)-N—benzylamino]-ethyl}-benzylamine and 4-benzyloxyphenacyl bromide | 95 |
| (i) 1-phenyl-2-{2-[(1,3,5-trimethylpyrazol-4-yl)-N—benzylamino]-ethyl-N—benzylamino}-ethanone from N—{2-[(1,3,5-trimethylpyrazol-4-yl)-N—benzylamino]-ethyl}-benzylamine and phenyacyl bromide | 98 |
| (j) 1-(3-benzyloxyphenyl)-2-[2-(1,4-dimethylpyrazol-5-ylamino)-ethyl-N—benzylamino]-ethanone from N—[2-(1,4-dimethylpyrazol-5-ylamino)-ethyl]-benzylamine and 3-benzyloxyphenacyl bromide | 100 |
| (k) 1-(4-benzyloxyphenyl)-2-[2-(1,4-dimethylpyrazol-5-ylamino)-ethyl-N—benzylamino]-ethanone from N—[2-(1,4-dimethylpyrazol-5-yl-amino)-ethyl]-benzylamine and 4-benzyloxyphenacyl bromide | 92 |
| (l) 1-(3-benzyloxyphenyl)-2-[2-(indazol-4-ylamino)-ethylamino]-ethanone from 2-(indazol-4-ylamino)-ethylamine and 3-benzyloxyphenacyl bromide | 94 |
| (m) 1-(4-benzyloxyphenyl)-2-[2-indazol-4-ylamino)-ethyl-N—benzylamino]-ethanone from N—[2-(indazol-4-ylamino)-ethyl]-benzylamine and 4-benzyloxyphenacyl bromide | 85 |

EXAMPLE 9

Tablets are produced, each of which contains 10 g. α-{[2-(3-nitrophenylamino)-ethyl]-aminomethyl}-phenylmethanol. The tablets are produced with the following formulation:

| | |
|---|---|
| α-{[2-(3-nitrophenylamino)-ethyl]-aminomethyl}-phenylmethanol | 10 g. |
| lactose | 80 g. |
| starch | 29 g. |
| magnesium stearate | 1 g. |

The above-mentioned active compound is finely pulverised and mixed with the lactose and starch. The mixture is then granulated in conventional manner. The magnesium stearate is added to the granulate and the mixture is pressed to give 1000 tablets, each having a weight of 0.12 g.

A test of the inotropic effect of the compounds according to the invention was made by way of the measurement of hemodynamics. The haemorheological effect was also determined.

HEMODYNAMICS

For the investigations mixed-bred dogs of both sexes were used which in a preparatory operation under aseptic conditions had been implanted with catheters in the A. and V. femoralis and through the myocardium in the left ventricle. Not before 10 days after this operation, when the animals were once again in a clinically healthy state, were the tests begun.

During the entire test, the animals were in the conscious state. The arterial blood pressure was recorded continually through the catheter with an electromechanical pressure transducer. In addition, by means of a pressure recorder (tipmanometer) which was introduced into the ventricle catheter and pushed right up to the heart, the pressure in the left ventricle was continually measured and from it, by differentiation with respect to time ($dp/dt_{max}$) the heart output was determined. The heart rate was calculated by counting the heart action with rapid paper advance over a predetermined time of measurement. Through puncture electrodes, the ECG for recognizing arrhythmias and extrasystoles was obtained. All parameters were recorded on a direct recorder (made by Schwarzer).

The doses were i.v. administered cumulatively in a range between 1 and 256 mcg/kg. 10 minutes after each administration of the compound, $dp/dt_{max}$, the heart frequency and the mean blood pressure were determined.

For the determination of the effect of the substance, the regression line was computed from the logarithm of the dose and $dp/dt_{max}$. From it, the dose at which the starting values increased 50% was interpolated.

To exemplify the inventive compounds the effects of 25 representative inventive compounds were measured and the results entered in Table 1. As a rule the heart frequency rose while the blood pressure dropped.

RHEOLOGY to be responsible for the reduction of the flow shear stress.

LITERATURE

1. H. Radtke:
Determination of the flow shear stress of blood and erythrocyte suspension in a capillary viscosimeter with y-shaped branching. Dissertation at the RWTH Aachen, West Germany (1982).

2. H. G. Roogenkamp: F. Jung; H. Kiesewetter:
Apparatus for the electrical measurement of the deformability of erythrocytes. Biomed. Tech. 28, 100-104 (1983)

3. H. Kiesewetter: H. Radtke; R. Schneider; K. Mussler; A. Scheffler; H. Schmidt-Schonbein:
The Mini erythrocyte aggregometer: A new device for rapid quantification of the extent of erythrocyte aggregation. Biomed. Tech. 27, 209-213 (1982).

TABLE 1

PHARMACOLOGICAL DATA
$DE_{150\%}$ = required dose to increase $dp/dt_{max}$ 50% relative to the starting value

| Compound Example | $DE_{150\%}$ (mcg/kg) |
|---|---|
| (6j) | 1.36 |
| (6n) | 11.5 |
| (6c) | 15.9 |
| (5) | 28.9 |
| (6a) | 275.9 |
| (6b) | 3.8 |

TABLE 2

RHEOLOGICAL DATA
Mean value ± standard decrease (of 3 patients)

| Flow shear stress (mPa) | | | Mean passage time (msec) | | | Aggregation index | | |
|---|---|---|---|---|---|---|---|---|
| control | Example 6c) | Example 6c) | control | Example 6c | Example 6c | control | Example 6c | Example 6c |
| 0.3 ± 0.08 | 0.04 ± 0.08 | 0.09 ± 0.08 | 18.8 ± 3.5 | 14.8 ± 1.6 | 16.2 ± 4.1 | 14.8 ± 3.2 | 14.4 ± 3.6 | 15.5 ± 2.7 |

The rheology investigations were carried out in vitro with the following three methods. The flow shear stress was determined with the erythrocyte stasis apparatus (1). Using a selecting erythrocyte rigidometer (SER), on a membrane with a single hole, the erythrocyte passage time was measured (2). As a measure of the aggregation tendency of the erythrocytes, the erythrocyte aggregation index was determined by means of an aggregometer (3). All investigations were conducted with the blood of patients with peripheral circulatory disorders (stage 2 according to Fontaine). Two erythrocyte suspensions were prepared with a hematocrit of 45%. One contained only the corresponding volume in solvent, while the other contained the inventive compound to be tested. The compound concentration was $10^{-8}$ mol/l for each test. After 30 minutes of incubation, the rheological investigations were conducted.

The results of this testing is presented in Table 2. It shows that without appreciably changing the erythrocyte aggregation index the flow shear stress and the erythrocyte rigidity are reduced by the inventive compounds.

Therefore, the inventive compounds are not only positively inotropic, but they also reduce the blood viscosity, which expresses itself in a reduced flow shear stress. A parameter responsible for these effects is erythrocyte deformability. Our results therefor show that the rigidity of the erythrocytes of the patients is reduced. But since the aggregation tendency remains unchanged, the improvement of erythrocyte deformability appears It will be understood that the specification and examples are illustrative but not limitative of the present invention and that other embodiments within the spirit and scope of the invention will suggest themselves to those skilled in the art.

What is claimed is:

1. An aminoalcohol of the formula:

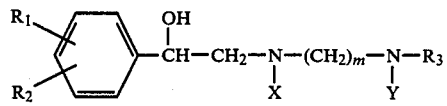

wherein
R$_1$ and R$_2$ are individually selected from the group consisting of hydrogen, hydroxyl, C$_1$-C$_4$ alkoxy, benzyloxy, C$_1$-C$_4$-alkoxycarbonyl, C$_1$-C$_4$-alkanesulphonamido;

m is 2, 3 or 4;

X is hydrogen or benzyl;

Y is hydrogen or benzyl; and

R$_3$ is phenyl substituted twice by C$_1$-C$_6$-alkyl, nitrophenyl, aminophenyl, 1,3,5-tri-C$_1$-C$_6$-alkyl-2,4-dioxo-1H,3H-pyrimidin-6-yl, indolyl, indazolyl, benzimidazolyl, 1,4-di-C$_1$-C$_6$-alkyl pyrazol-5-yl or a group of the formula

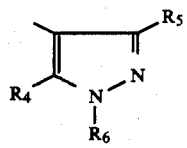

wherein R₄ is $C_1$–$C_4$ alkyl, R₅ is $C_1$–$C_4$-alkyl and R₆ is a $C_1$–$C_6$-alkyl, $C_2$–$C_6$ alkenyl, phenyl or benzyl or a pharmacologically acceptable salt thereof.

2. The aminoalcohol of claim 1 wherein R₃ is phenyl substituted twice by $C_1$–$C_6$-alkyl.

3. The aminoalcohol of claim 1 wherein R₃ is the group of the formula

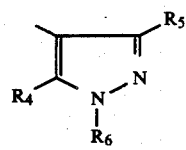 (Q)

wherein R₄, R₅ and R₆ are as defined in claim 1.

4. The aminoalcohol of claim 1 wherein Y is hydrogen.

5. The aminoalcohol of claim 1 wherein Y is benzyl.

6. The aminoalcohol of claim 1 designated alpha-{[2-(2,6-dimethylphenylamino)-ethyl]-aminomethyl}-2-hydroxyphenylmethanol.

7. The aminoalcohol of claim 1 designated alpha-{[2-(2,6-dimethylphenyl-amino)-ethyl]-aminomethyl}-2-methoxyphenylmethanol.

8. The aminoalcohol of claim 1 designated alpha-{[2-(2,6-dimethylphenyl-amino)-ethyl]-aminomethyl}-4-hydroxy-phenylmethanol.

9. The aminoalcohol of claim 1 designated alpha-{[2-(2,6-dimethylphenyl-amino)-ethyl]-aminomethyl}-3-hydroxyphenylmethanol.

10. The aminoalcohol of claim 1 designated 4-hydroxy-alpha-{[2-(1,3,5-trimethylpyrazol-4-ylamino)-ethyl]-aminomethyl}-phenoylmethanol.

11. The aminoalcohol of claim 1 designated 3-hydroxy-alpha-{[2-(indazol-4--ylamino)-ethyl]-aminomethyl}-phenylmethanol.

12. A method for treating heart and circulatory diseases which are susceptible to an increase in the deformability of erythrocytes in the blood or to a positive inotropic action comprising administering an amount of the aminoalcohol of claim 1 sufficient to increase the deformability of erythrocytes in the blood or to induce a positive inotropic action.

13. A method as in claim 12 comprising administering an amount of said aminoalcohol sufficient to increase the deformability of erythrocytes in blood.

14. The method of claim 13 wherein 0.5 to 40 mg per kg body weight per day are administered.

15. A pharmaceutical composition comprising a pharmaceutically acceptable carrier containing an effective amount for administration to a patient to increase erythrocyte deformation, of an aminoalcohol of claim 1.

* * * * *